United States Patent [19]
Schlau

[11] 4,312,213
[45] Jan. 26, 1982

[54] MEASURING CELL FOR DETECTING THE CONCENTRATION OF $UF_6$ IN $H_2$

[75] Inventor: Peter Schlau, Frankfurt, Fed. Rep. of Germany

[73] Assignee: Hartman & Braun Aktiengesellschaft, Frankfurt, Fed. Rep. of Germany

[21] Appl. No.: 93,294

[22] Filed: Nov. 13, 1979

[30] Foreign Application Priority Data

Nov. 11, 1978 [DE]  Fed. Rep. of Germany ....... 2849033

[51] Int. Cl.³ .......................................... G01N 27/04
[52] U.S. Cl. ................................................. 73/27 R
[58] Field of Search ..................................... 73/27 R

[56] References Cited

U.S. PATENT DOCUMENTS 2,329,840  9/1943  Keinath .............................. 73/27 R
3,040,561  6/1962  Wright ................................ 73/27 R

OTHER PUBLICATIONS

T. Tsujino et al., "In-Line Gas Analyzer for $UF_6$ and $F_2$ Through Differential Thermal Conductivity Measurements", *Journal of Nuclear Science and Technology*, vol. 10, No. 2, pp. 118-124, Feb. 1973.

*Primary Examiner*—Stephen A. Kreitman
*Attorney, Agent, or Firm*—Smyth, Pavitt, Siegemund & Martella

[57] ABSTRACT

Four corrosion-proof steel tubes are arranged in a circle, two of the steel tubes serving as reference chamber, the other two being serially flown through by a measuring gas. Each cell contains centrally a heating coil of nickel on a PTFE mandrel held by an electrode which is fed through a brazed on ceramic insulation in the top portion of the respective chamber. The other electrode is fed through off center; each electrode is hollow in the feed-through.

3 Claims, 2 Drawing Figures

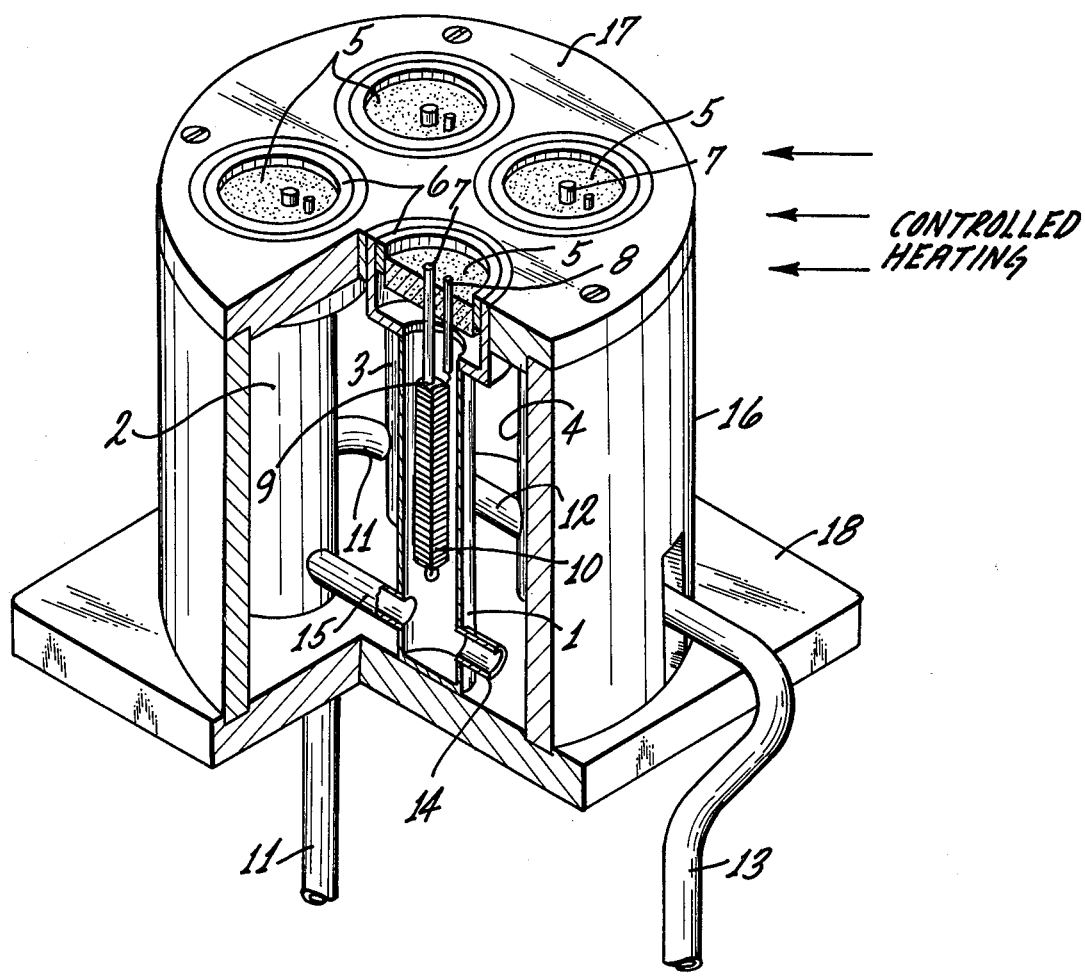
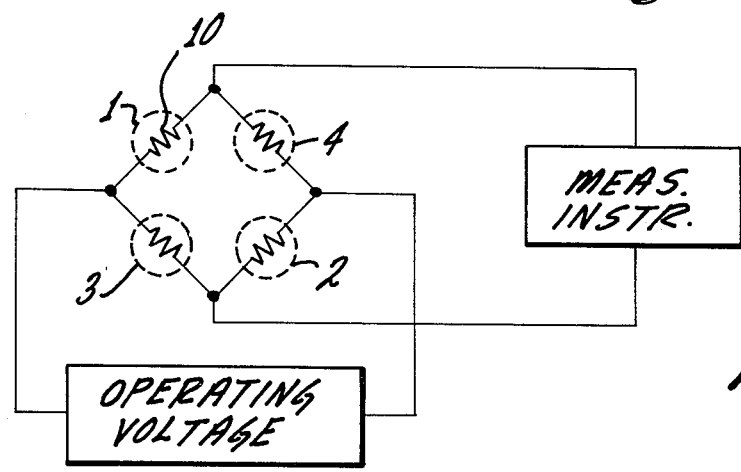

MEASURING CELL FOR DETECTING THE CONCENTRATION OF UF₆ IN H₂

BACKGROUND OF THE INVENTION

The present invention relates to an apparatus for indirectly measuring the concentration of $UF_6$ in $H_2$ by means of measuring the thermal conductivity of the carrier gas ($H_2$) containing $UF_6$.

The U.S. Pat. No. 2,329,840 describes a measuring device for detecting $CO_2$ and $H_2$, in which four chambers are provided as bores in a metal block. The gas to be analyzed is fed into two of these chambers; the two other ones contain a reference gas. The chambers are heated by means of electrical wires. The thermal conductivity of the gas to be analyzed depends upon the concentration of, e.g., $CO_2$ therein.

This property is used by determining the heat flow from a heated wire into the surrounding gas. On the basis of the four chambers, one provides four such wires and connects them in a bridge circuit; and differences in the thermal conductivity of the gases surrounding the wires imbalances in the bridge. Upon proper adjustment, the bridge voltage is, in fact, a representation of the concentration to be measured.

It could be deemed obvious to use such a cell system for determining $UF_6$ in $H_2$. Generally speaking, there is a need in the field of atomic engineering, particularly in the field of Uranium enrichment, to measure the concentration of $UF_6$ in a carrier gas. It was found, however, that the known devices of the type described do not perform satisfactorily. The reason for this is that even a minor and spurious presence of water vapor renders $UF_6$ very aggressive and the cells corrode reapidly.

Aside from the foregoing, an analysis of the problem at hand has revealed that the measuring equipment needed for detecting $UF_6$ in hydrogen must possess these properties: (1) It must be highly insensitive to pressure variations in the operating range which extends from approximately 200 millibars to approximately 300 millibars. (2) The passage ways for the gas must be tightly sealed; in terms of leakage rate values, they must not exceed $10^{-8}$ mbar l/s. (3) The device must operate rather independantly from particulars of the gas flow. (4) Reaction response to changes in concentration must be high (for example, the time of response to a 90% concentration must be below one minute). (5) The device must operate with little dependency upon ambient temperature. (6) The measurement must yield stable outputs.

DESCRIPTION OF THE INVENTION

It is an object of the present invention to provide a new and improved measuring cell or device for detecting $UF_6$ in $H_2$ on the basis of thermal conductance from heating wires into measuring and reference gases, and fulfilling all the aforementioned requirements.

It is a particular object of the present invention to improve a measuring device of the type referred to above, and in which four chambers are arranged in a circle, two for measuring gas, two for reference gas, and each containing heating wires exposed to the gas in the respective chamber. The improvements must relate to the specific use of such a cell for measuring $UF_6$ in $H_2$.

In accordance with the preferred embodiment of the invention, it was discovered that corrosion-proof steel, when used for tubes establishing the four chambers, and when combined with a particular ceramic feed-through construction for electrodes and mounting thereof, should be combined further with a particular arrangement and construction of the heating wires in the chambers.

The preferred embodiment of the invention, the objects and features of the invention, and further objects, features and advantages thereof, will be better understood from the following description taken in connection with the accompanying drawings.

DESCRIPTION OF THE DRAWINGS

FIG. 1 is a perspective view of and into a measuring cell system, being shown partially cut open and constructed in accordance with the preferred embodiment of the invention; and FIG. 2 shows schematically the four heating wires of the cell system of FIG. 1, connected in a measuring circuit.

Proceeding now to the detailed description of the drawings, the figures show four tubular chambers 1, 2, 3, and 4 constructed from corrosion-proof, e.g., stainless-steel-type tubing. In particular, each of the tubes is closed at the bottom and has a wider portion, such as 1a mounted on top of the tube.

The tubular chamber 1 is shown cut open, revealing the fact that the top closure 5 of the tubes is a feed-through-type insulator. This insulating material is an $Al_2O_3$-based ceramic deposited on and in a metal collar, annulus, or ring 6. Ring 6 is made of a nickel-iron alloy and is brazed to the ceramic to obtain a gas-tight seal.

Annulus 6 is welded to the respective tube of which the chamber is made, particularly to the wider portion on top of the respective tube, such as 1a of the cut-open tube. The brazing mixture or hard solder is protected by a cover of nickel.

Rod-like electrodes 7 and 8 are partially embedded for feed-through in insulators 5, whereby one electrode (e.g., 7) is in each instance centrally mounted. This central mounting is externally visible by a central projection of the upper end of an electrode 7 above the respective disk-shaped insulation 5. On the other hand, electrode 7 runs in the respective axis of the tube into whose interior the electrode extends.

Electrode 7 carries in each instance a winding mandrel 9 of a star-shaped cross section which, in turn, carries a nickel wire 10, serving as a heating coil. The mandrel or holder 9 is made of polytetrafluoroethylene. The ends of wire 10 are welded to electrodes 7 and 8 in the respective chamber. It will be appreciated that each chamber, 1 through 4, contains such an assembly; the electrode ends, as they project from the chambers, are visible in all four cases. As shown in FIG. 2, the four wires 10 in the four chambers 1, 2, 3, and 4 are connected in a bridge circuit, which is conventional and does not require elaboration.

Electrodes 7 and 8 are all made of nickel, or are nickel-plated; and they are connected to the respective ceramic cover 5, just as the respective annulus 6 is connected thereto to obtain air-tight sealing. Electrodes 7 and 8 should be hollow in the feed-through zone, so that thermally induced stress and strain in the material does not interfere with the gas-tight seal. The hollow configuration of at least a portion of the electrodes enhances the radial elasticity of the electrodes.

The two chambers 3 and 4 are passed through by measuring gas to be analyzed. Accordingly, an inlet pipeline 11, or the like, is connected to chamber 3; a duct 12 interconnects chamber 3 and 4, and the gas is discharged from chamber 4 by means of a duct 13. All of these conduits 11, 12, and 13 are made of corrosion-proof steel. The connections are made in that all three conduits are connected to the respective chamber tubes near the bottom thereof, particularly underneath the heating coils, 10, therein. The conduits are welded to the respective chamber tubes.

The two chambers 1 and 2 are filled with hydrogen, which serves as a reference gas. A short tube 15 interconnects the two chambers 1 and 2, and the form is additionally provided with an inlet nipple 14 through which the two chambers 1 and 2 are filled with the reference gas.

The entire assembly of chambers and tubes is contained and/or mounted to a cylindrical vessel made of a short metal tube 16 and of a top cover 17. Cover 17 is provided with four apertures, arranged around the center of cover disk 17, and the annuli 6 are welded to these apertures for being mounted therewith to cover plate or disk 17. These apertures provide also access to the, all together eight, electrodes 7 and 8, to be interconnected electrically in the bridge circuit, as shown in FIG. 2, or otherwise.

Tubular chambers 1 to 4 sit all on a bottom plate 17 of the vessel, having an annular recess in which the bottom part of tube 16 has been inserted.

The device is operated in the temperature-controlled environment; that is to say, vessel 16-17-18 is surrounded by a constant temperature medium. The constant temperature is obtained by means of suitably heating the environs of the vessel in combination with a thermofeeder and a controller (not shown).

Conceivably, the external heating and temperature control, based on a locally effective thermostat, does not provide a truly isothermic environment. However, the metal cylinder and its coverplates are particularly provided as good heat conductors to establish isothermic conditions in the interior of the vessel, and the various chambers, even if the outside is not completely isothermic.

It has been found that the cell fulfills all of the requirements listed above. The sensitivity is so extensive that the operating temperature of the heating wires 10 can be relatively low, not more than 100° C. This low temperature operation enhances further the corrosion resistance of the cell against the measuring gas.

The invention is not limited to the embodiments described above, but all changes and modifications thereof not constituting departures from the spirit and scope of the invention are intended to be included.

I claim:

1. An apparatus for detecting the concentration of $UF_6$ in $H_2$, comprising:
   a plurality of four individual tubes establishing respectively four tubular chambers, each of said tubes being made of corrosion-proof steel, said four tubes being arranged in a circle;
   a plurality of nickel iron alloy annuli respectively welded peripherally to one end each of the four tubular chambers;
   feed-through insulators based on an $Al_2O_3$ ceramic material, respectively brazed to said nickel iron alloy annuli;
   a nickel layer on brazing material of the respective insulator-to-annulus connection;
   a plurality of four heating conductors made of nickel and respectively contained in the chambers;
   nickel or nickel-plated electrodes for connection to the conductors and being fed through said ceramic material insulators;
   a plurality of mandrels, there being one of said mandrels in each of the chambers for respectively supporting the conductors in a coiled configuration, the mandrels of the plurality being respectively centrally disposed in the tubular chambers, one of the electrodes supporting the mandrel and being centrally fed through the respective insulator;
   means for mounting said tubular chambers in the circular arrangement;
   means for feeding measuring gas to two of the chambers, the others containing a reference gas; and
   circuit means including a measuring instrument for interconnecting the four heating conductors.

2. An apparatus as in claim 1, said electrodes being hollow at least in a zone of traversal of the respective insulator.

3. An apparatus as in claim 1 or 2, wherein said mandrels are made of polytetrafluoroethylene and are of a star-shaped cross section.

* * * * *